United States Patent [19]

McMahon et al.

[11] Patent Number: 5,712,011
[45] Date of Patent: Jan. 27, 1998

[54] TUG-RESISTANT LINK

[75] Inventors: Thomas A. McMahon, Wellesley, Mass.; Stephen N. Robinovitch, San Francisco, Calif.; Wilson C. Hayes, Lincoln, Mass.

[73] Assignees: Beth Israel Deaconess Medical Center, Inc., Boston; President and Fellows of Harvard College, Cambridge, both of Mass.

[21] Appl. No.: 660,759

[22] Filed: Jun. 6, 1996

Related U.S. Application Data

[60] Provisional application No. 60/000,015 Jun. 8, 1995.

[51] Int. Cl.⁶ .................... B32B 3/00; A41F 1/00
[52] U.S. Cl. .................. 428/36.9; 2/338; 24/31 R; 24/305
[58] Field of Search .................. 2/338; 24/31 R, 24/305; 428/36.9

[56] References Cited

U.S. PATENT DOCUMENTS

| | | | |
|---|---|---|---|
| 3,438,674 | 4/1969 | Radke et al. | 297/386 |
| 3,445,559 | 5/1969 | Siteman | 264/263 |
| 3,583,530 | 6/1971 | De Venne | 188/1 |
| 3,596,972 | 8/1971 | Pool | 294/103 |
| 3,601,923 | 8/1971 | Rosenberg | 46/151 |
| 3,833,952 | 9/1974 | Rosenberg | 5/353 |
| 3,848,802 | 11/1974 | Degginger et al. | 239/10 |
| 3,889,969 | 6/1975 | Otani | 280/150 |
| 4,054,952 | 10/1977 | Swallow | 2/338 |
| 4,069,545 | 1/1978 | Holet et al. | 16/49 |
| 4,169,336 | 10/1979 | Kuhn | 46/156 |
| 4,211,308 | 7/1980 | Reuterskoild | 188/1 |
| 4,212,747 | 7/1980 | Swanson | 252/8.55 R |
| 4,242,380 | 12/1980 | Courtoy | 427/366 |
| 4,371,636 | 2/1983 | Distler et al. | 523/223 |
| 4,442,241 | 4/1984 | Drake et al. | 523/130 |
| 4,471,538 | 9/1984 | Pomeranz et al. | 36/28 |
| 4,518,335 | 5/1985 | Pujari | 425/78 |
| 4,536,539 | 8/1985 | Lundberg et al. | 524/521 |
| 4,584,339 | 4/1986 | Lundberg et al. | 524/516 |
| 4,622,166 | 11/1986 | Nakazawa et al. | 252/313.1 |
| 4,654,396 | 3/1987 | Bung et al. | 524/401 |

(List continued on next page.)

FOREIGN PATENT DOCUMENTS

| | | | |
|---|---|---|---|
| 1003320 | 1/1977 | Canada | 156/16 |
| 2457084 | 12/1980 | France | A44C 5/20 |
| 1 256 554 | 12/1967 | Germany . | |
| 1 531 512 | 7/1970 | Germany | A62B 35/00 |
| 2 249 732 | 4/1974 | Germany | A62B 35/00 |
| 31 48 888 AI | 6/1983 | Germany | F16D 35/00 |
| 34 05 907 A1 | 8/1985 | Germany | F16F 13/00 |
| 39 15 115 C1 | 1/1991 | Germany | F16F 13/00 |
| 60-023646 | 2/1985 | Japan | F16F 9/30 |
| 60-065930 | 4/1985 | Japan | F16F 15/02 |
| 1 247 582 | 9/1971 | United Kingdom | F16B 11/00 |
| 1 399 096 | 6/1975 | United Kingdom | A62B 35/00 |
| 1 436 701 | 5/1976 | United Kingdom | F16F 7/08 |
| 2 009 588 | 6/1979 | United Kingdom | A62B 35/00 |
| 2 048 430 | 12/1980 | United Kingdom | F16F 7/12 |
| WO 94/12066 | 6/1994 | WIPO | A41D 31/00 |

Primary Examiner—Richard Weisberger
Attorney, Agent, or Firm—Bromberg & Sunstein LLP

[57] ABSTRACT

A tug-resistant unit in which the first and second relatively inextensible members overlap one another. A shear-thickening composition having dilatant flow characteristics is disposed between the first and the second inextensible members. The composition provides a variable resistance to linear movement of the second inextensible member relative to the first inextensible member as a function of the shear forces exerted upon the dilatant fluid. The inextensible members may be enclosed within an extensible enclosure to form an elastic strap. Alternatively, one inextensible member may form a portion of the enclosure while the second inextensible member is disposed within the strap so as to overlap the first inextensible portion of the enclosure. The strap provides low resistance to slowly-varying tensile forces and high resistance to rapidly-changing tensile forces, thereby moderating the velocity of relative motion between the ends.

57 Claims, 12 Drawing Sheets

U.S. PATENT DOCUMENTS

| | | | |
|---|---|---|---|
| 4,759,428 | 7/1988 | Seshimo | 188/312 |
| 4,820,380 | 4/1989 | O'Callaghan et al. | 162/135 |
| 4,825,983 | 5/1989 | Nakanishi | 188/378 |
| 4,852,533 | 8/1989 | Doncker et al. | 123/192 |
| 4,854,344 | 8/1989 | Schnipke | 137/606 |
| 4,892,551 | 1/1990 | Haber | 623/23 |
| 5,037,880 | 8/1991 | Schmidt et al. | 524/823 |
| 5,078,562 | 1/1992 | DeHaitre | 411/302 |
| 5,138,722 | 8/1992 | Urella et al. | 2/209 |
| 5,139,240 | 8/1992 | Miyamoto et al. | 267/140.13 |
| 5,220,975 | 6/1993 | Zimmer et al. | 180/197 |
| 5,246,654 | 9/1993 | Ertle et al. | 264/118 |
| 5,450,931 | 9/1995 | Masuda | 188/268 |
| 5,501,434 | 3/1996 | McGuire | 267/140.11 |

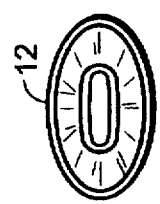
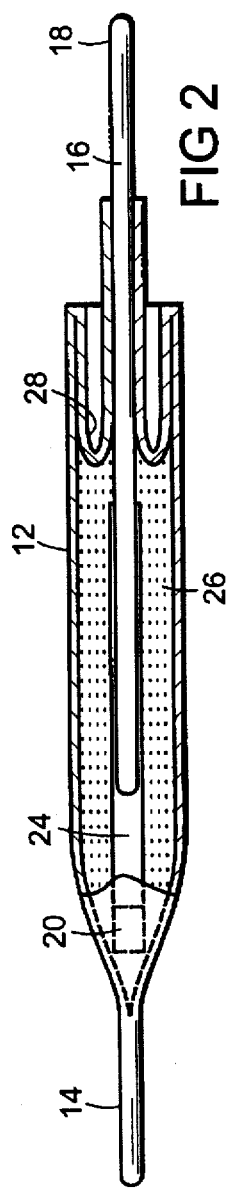
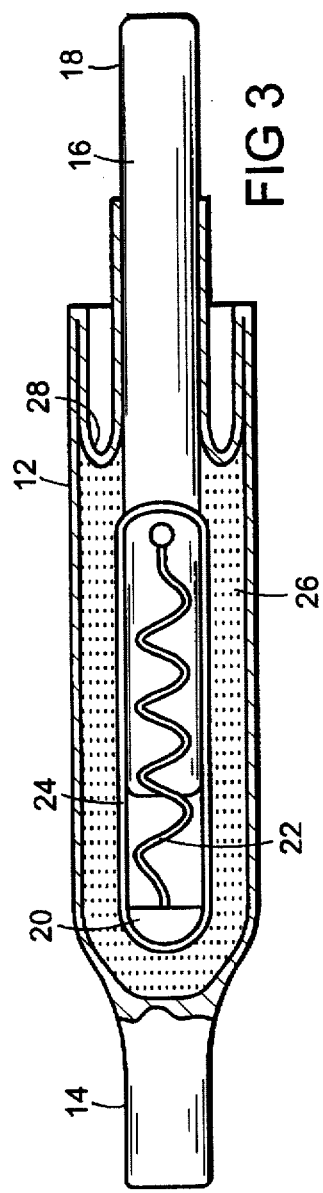
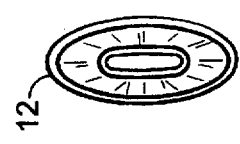
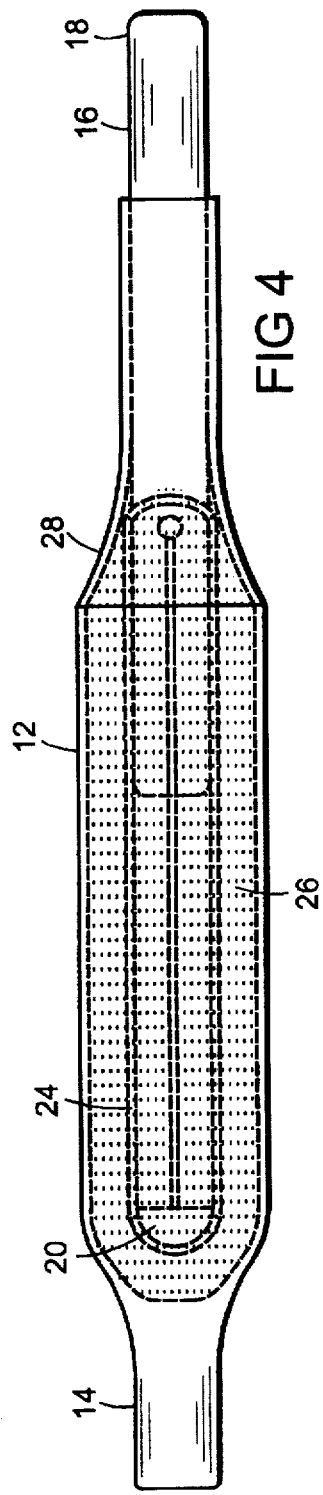

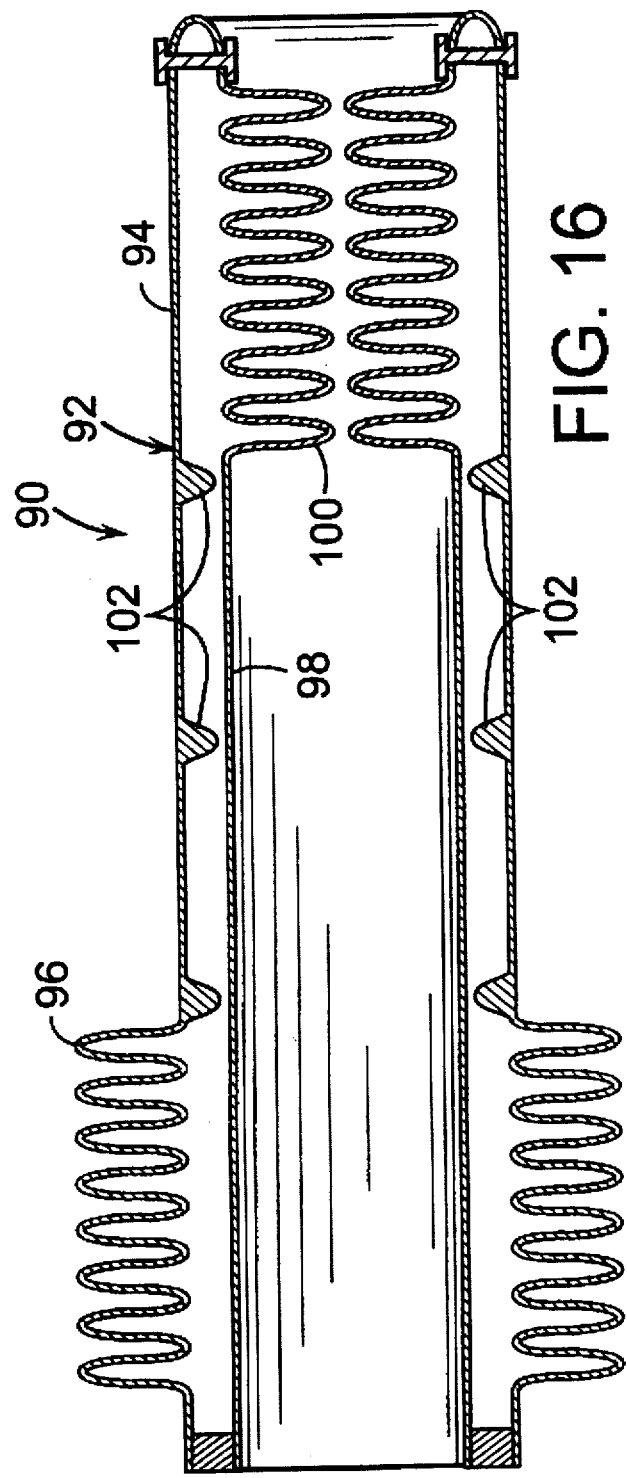

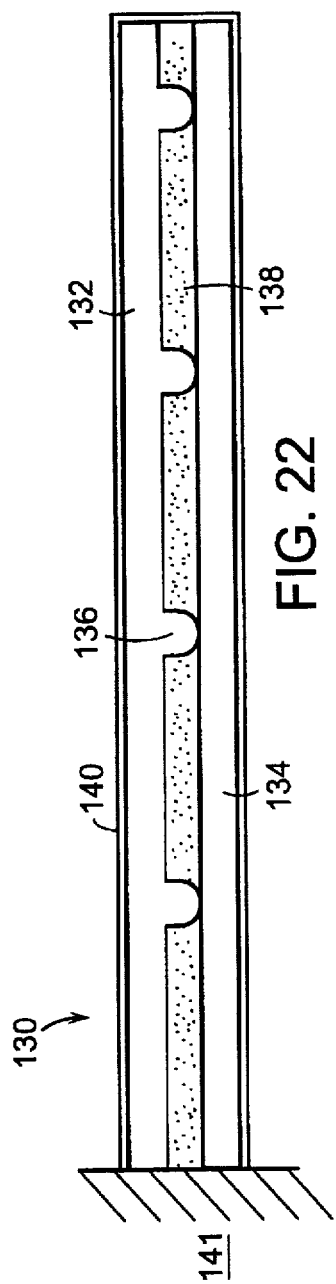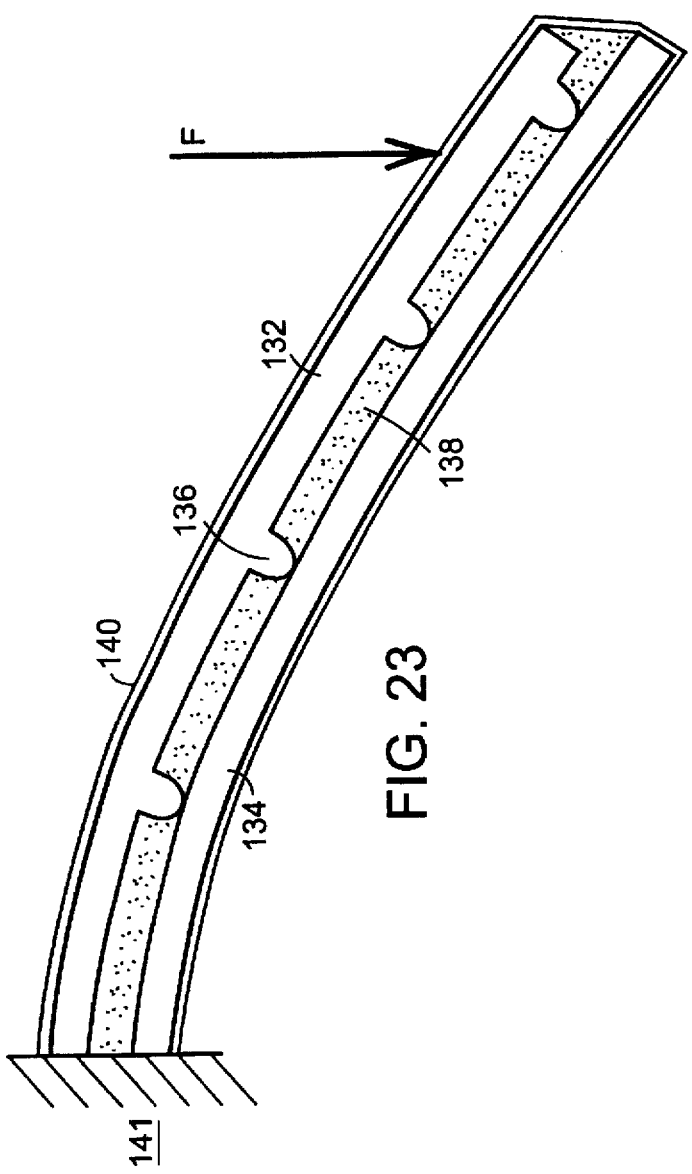

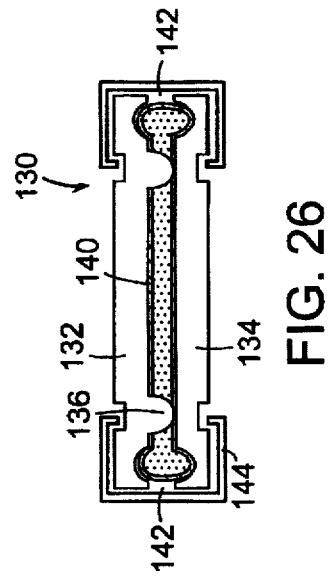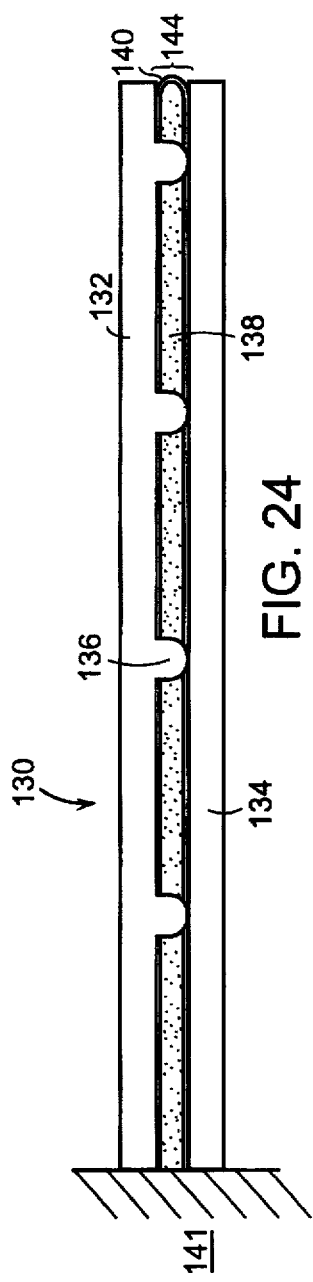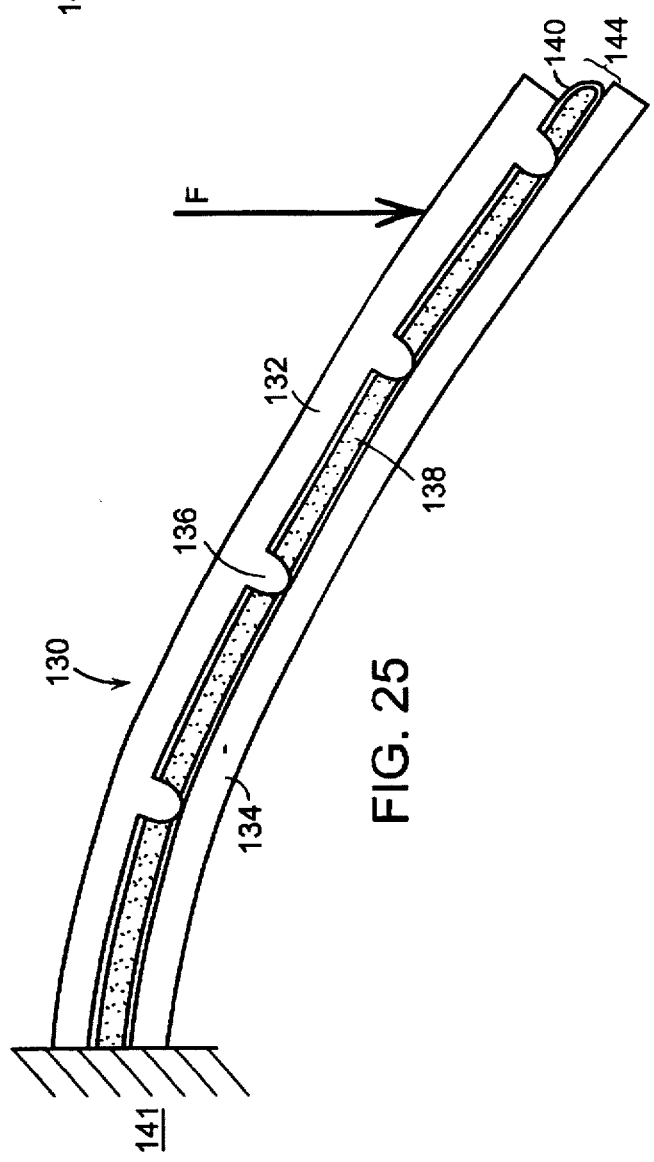

TUG-RESISTANT LINK

DESCRIPTION

This application claims priority from U.S. Provisional Application No. 60/000,015, filed Jun. 8, 1995, which is hereby incorporated herein by reference.

TECHNICAL FIELD

The present application relates to a link, strap, beam, joint or hinge. In particular, the invention is directed to a connecting link, strap, beam, joint or hinge that behaves elastically under slowly-varying loads but provides a high-viscosity response when subject to large rapidly-increasing loads.

BACKGROUND ART

There are countless applications, particularly in the sports arena, where straps or connecting links are used. More particularly, such straps or links may be of enhanced value if they were elastic to slowly-varying loads, so that they could be worn comfortably during normal playing motions, yet relatively rigid in response to the rapidly-increasing high loads associated with impacts. For example, the chin straps on helmets for football, baseball, soccer, ice hockey, motorcycling, snowmobiling, bicycling, horseback riding, etc., would offer enhanced protection if provided with such properties. Straps used for closing a foot into a shoe or boot that resisted rapid inversion motions of the foot could help prevent inversion sprains caused by rapid, large inversion movements applied to the foot during sports activity. Straps, joints or hinged devices for use in protective appliances such as rib protectors, shoulder pads, elbow pads, knee pads and pants used primarily in football and ice hockey would also benefit from a device that would permit movement of one semi-rigid shell-like element with respect to another during normal playing motions, but would behave like a rigid link, keeping the shell elements from moving significantly with respect to each other, on impact. For appliances such as knee braces, wrist and elbow stiffeners and cervical collars, if such straps or hinges were made available, they would reduce the risk of injury through hyperextension or other non-physiological joint motions.

A yielding response to slowly-varying loads and a rigid response to large, rapidly-increasing loads can be found in the inertial reel in shoulder strap and seat belt restraint mechanisms in automobiles, aircraft and trucks. However, the straps themselves are generally inextensible. An inertial reel mechanism provides resistance to rapidly-increasing loads using the centrifugal force associated with weights on a spinning disk. The present invention reaches a similar goal using an entirely different mechanism, the property of increasing viscosity with increasing shear rate in a shear-thickening composition exhibiting a dilatant flow.

SUMMARY OF THE INVENTION

The present invention is directed to a tug-resistant unit in the form of a link, a strap or the like. The invention advantageously opposes relatively slow translational motions with a relatively weak force while opposing rapid motions with a strong damping force. In general, the tug-resistant unit of the present invention includes two overlapping inextensible members. A shear-thickening composition exhibiting a dilatant flow property is disposed between the two inextensible members. An extensible member such as an elastic envelope or membrane completes an enclosure to hold the shear-thickening composition therein. Slowly pulling one end of the unit produces a slow sliding motion between the overlapping inextensible members. Therefore, when the pulling force rises slowly, the unit extends slowly because the viscous force resisting the sliding motion between the inextensible members is small. However, when the pulling force rises rapidly, the unit lengthens only slowly, because the shear-thickening composition between the inextensible members displays a high viscosity when an attempt is made to slide the inextensible members rapidly past one another.

In accordance with a presently preferred embodiment of the invention, a first inextensible member of the tug-resistant unit comprises an inextensible enclosure while a second inextensible member extends axially outward from within the enclosure. The inextensible member is coupled to one end of the enclosure by an inextensible cord. An elastic band further connects the second inextensible member to the one end of the inextensible enclosure. A shear-thickening composition exhibiting a dilatant flow property is disposed within the inextensible enclosure such that the composition is between the inextensible member and the enclosure. A flexible membrane is provided to hold the shear-thickening composition within the inextensible enclosure.

In accordance with an alternate embodiment of the invention, the tug-resistant unit includes an extensible enclosure having two elongated members attached thereto. A first member and a second member each includes an inextensible portion connected to the enclosure. The inextensible portions of the two members overlap. A shear-thickening composition is held within the extensible enclosure and between the inextensible portions of the two elongated members. Each of the members may additionally include an extensible portion extending from the inextensible portion. The extensible portions are positioned so that each is connected to an opposite point on the enclosure.

In a further embodiment of the invention, an elongated enclosure includes an inextensible portion and an extensible portion. An inextensible member is suspended within the elongated enclosure. At least one extensible link attaches an end of the inextensible member to the enclosure. The inextensible member is in overlapping relation with the inextensible portion of the enclosure at least when in a rest state. A shear-thickening composition is disposed about the inextensible member within the enclosure.

In another embodiment of the invention, two plates are disposed within an extensible enclosure. The plates are substantially parallel to one another and are separated by a shear-thickening composition. A ring is provided at the periphery of the enclosure to maintain an extension of the enclosure over the plates.

Another embodiment of the tug-resistant unit includes a rigid ball that is disposed within a substantially spherical enclosure. An elongated member extends from the ball through an opening in the enclosure so that, when a force is applied to the member, the ball may pivot within the enclosure. A shear-thickening composition is provided within the unit between the enclosure and the ball.

Embodiments of the invention advantageously prevent or attenuate rapid extensional, translational or rotational motions and are flexible, lightweight, simple and inexpensive to manufacture. The extensible members of the invention return the tug-resistant unit to its original length under elastic forces after an applied load has been released. The transition between preventing linear extensional motion at high velocity and allowing extension at lower velocity is a range that can be predetermined by the geometry and physical parameters of the components of the tug-resistant unit. Other objects and advantages of the invention will become apparent during the following description of the presently preferred embodiments of the invention taken in conjunction with the drawings.

BRIEF DESCRIPTION OF THE DRAWINGS

FIG. 2 is a cross-sectional side view of the strap of FIG. 1 in a resting state.

FIG. 3 is a cross-sectional top view of the strap of FIG. 1 in a resting state.

FIG. 4 is a top view of the strap of FIG. 1 in a stretched state.

FIG. 5 is an end view of the strap of either FIG. 2 or FIG. 3.

FIG. 6 is an end view of the strap of FIG. 4.

FIG. 16 is a cross-sectional view of an alternate cylindrical link embodiment of the invention in a rest state.

FIG. 22 is a cross-sectional view of an embodiment of the invention employing two beams, shown under no load.

FIG. 23 is a cross-sectional view of the embodiment of FIG. 22, shown deflected under a transverse load F.

FIG. 24 is a cross-sectional view of an alternate embodiment of FIG. 22, shown under no load.

FIG. 25 is a cross-sectional view of the embodiment of FIG. 24, shown deflected under a transverse load F.

FIG. 26 is a cross-sectional view of an alternate embodiment of FIG. 24.

DETAILED DESCRIPTION OF THE PREFERRED EMBODIMENTS

Figure 1:
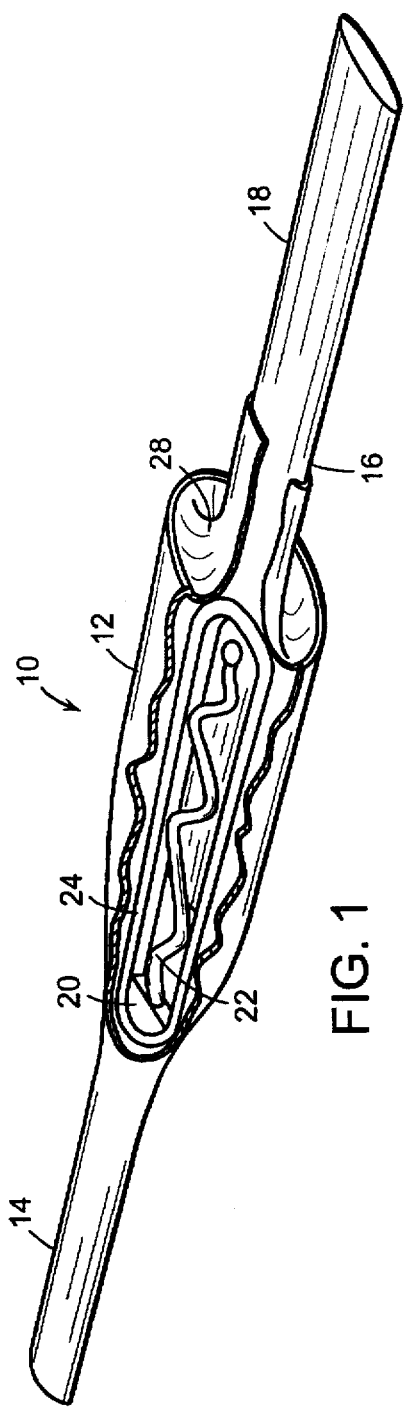
FIG. 1 is a partially broken-away perspective view of a tug-resistant unit of the present invention in the form of a strap.
Figure 7:
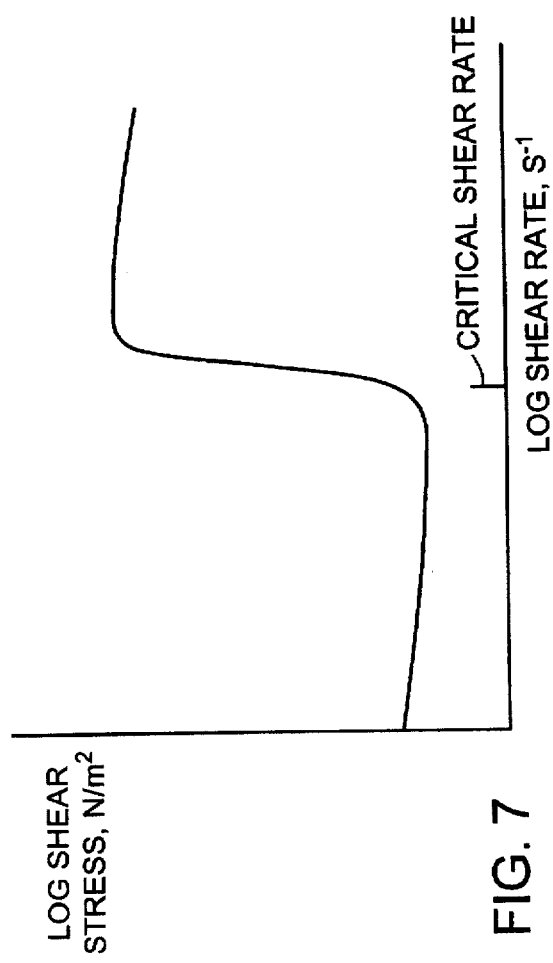
FIG. 7 is a schematic plot of shear stress versus shear rate for a dilatant liquid.

Referring now to the drawings, FIG. 1 illustrates a tug-resistant unit in the form of a strap 10. In accordance with this presently preferred embodiment, strap 10 includes an elongated inextensible enclosure 12 tapering toward a first end 14 of the strap 10, and an inextensible member 16 extending outwardly from within the inextensible enclosure 12 to terminate in a second end 18 of the strap 10. As shown in FIGS. 2, 3 and 4, a shear-thickening composition 26 exhibiting a dilatant flow property similar to a dilatant fluid is provided within the inextensible enclosure 12 and around the inextensible member 16. A shear-thickening composition exhibiting a dilatant flow property is typically a non-Newtonian fluid with properties as shown in FIG. 7, that is, low viscosity at low shear rates and relatively high viscosity above a certain shear rate called the critical shear rate. By having such properties, in the presence of shear forces, the dilatant composition may thicken, i.e. its viscosity increases, unaccompanied by a measurable time dependence. In other words, a shear-thickening composition which exhibits a dilatant flow property has the ability to immediately increase its viscosity in response to a high shear stress, thereby limiting the velocity of its motion. In one embodiment of the invention, the shear-thickening composition 26 may be kept within the inextensible enclosure 12 by a flexible rolling membrane 28 situated about an end where the inextensible member 16 extends from within the inextensible enclosure 12.

Where the inextensible enclosure 12 begins to taper, a fixture 20 is provided within the enclosure 12. An inextensible element 22 extends from the fixture 20 and is secured to the inextensible member 16. The inextensible element 22 may be secured to the inextensible member 16 by any means well known in the art, examples of which may include but are not limited to, adhesive, tie-knot, screw, nail, or staple. An elastic band 24 is provided in combination with the inextensible element 22 and further connects the inextensible member 16 to the fixture 20. The combination of the inextensible element 22 and the elastic band 24 allows the inextensible member 16 and enclosure 12 to return to their respective positions after having been subject to translational movement. As seen from the perspective of FIG. 5, the inextensible enclosure 12 is substantially elliptical in shape. By providing the inextensible enclosure 12 with such a shape, a volume may be maintained between the inextensible member 16 and enclosure 12 for placement of the shear-thickening composition 26 therein.

When an extending force acts tending to pull the first end 14 and the second end 18 of strap 10 apart, the elastic band 24 connecting the inextensible member 16 to the fixture 20 stretches, as illustrated in FIG. 4, allowing the inextensible member 16 to slide relative to the length of the enclosure 12 in a shearing motion. As the extending force continues, the inextensible element 22, which does not stretch appreciably and which is preferably provided with a length which upon full extension does not allow the inextensible member 16 to move completely from the enclosure 12, acts to maintain a portion of member 16 within the enclosure 12. Once the strap 10 is fully extended, the substantially elliptical shape of the enclosure 12, as seen in FIG. 5, becomes flattened, as seen in FIG. 6. The flattening occurs because the volume within the enclosure 12 has been modified due to the withdrawal of inextensible member 16 and shear-thickening composition 26 from within the enclosure 12. When the end-to-end linear velocity of lengthening is low, the viscosity of the shear-thickening composition between the inextensible enclosure 12 and inextensible member 16 is low. Thus, the overall strap 10 behaves essentially as an elastic unit to provide the enclosure and member with translational movement relative to one another. However, when the end-to-end velocity of lengthening is large enough to cause the shear-thickening composition 26 between the inextensible enclosure 12 and inextensible member 16 to reach its critical shear rate, the viscosity of the composition increases many-fold to oppose the shearing motion between the enclosure and the member. This is the "locked" configuration of the strap 10 and it persists for many seconds or for as long as an elevated end-to-end tensile force is applied. To this end, the strap 10 provides low resistance to slowly-varying tensile forces yet a high resistance to rapidly varying tensile forces applied to the strap 10.

In one embodiment of the invention, the inextensible enclosure 12 and inextensible member 16 of the strap 10 are preferably made from a flexible material. A flexible inextensible material such as urethane, polyurethane, polyethylene, neoprene or vinyl rubber of relatively high durometer, in a range from 70 to 90 durometers, is presently preferred. The inextensible enclosure 12 and member 16 should have surfaces that are sufficiently rough so as not to slide by the shear-thickening composition when subject to the rapidly varying tensile forces. Scratching the surfaces of the enclosure 12 and the member 16 with sandpaper of 100 grit works well, but other roughnesses between 60 and 180 grit are also effective. Alternatively, the surfaces of the inextensible enclosure 12 and member 16 may be encrusted with a granular material such as polystyrene, polyurethane, polyethylene or other plastic beads or silica particles, each preferably having a diameter ranging from about 10 micrometers to about 100 micrometers. In addition, the inextensible enclosure 12 and the rolling membrane 28 is preferably impermeable to solvents, including water. An example of a solvent-impermeable material is plastic with a metallic coating, including aluminized Mylar®, polyethylene, or polyvinylchloride. The inextensible element 22, in one embodiment, is a thread made from a flexible material. The flexible material from which the thread is made preferably does not stretch appreciably, and may be braided nylon, Dacron®, a nylon monofilament, or other synthetic fiber thread. The inextensible element 22 may additionally be fabricated from the material from which the inextensible enclosure 12 and member 16 are made. The elastic band 24, on the other hand, may be constructed from an elastomeric material such as a latex rubber band. The dilatant composition, in contrast, may be formed from a non-aggregate suspension of polystyrene spheres in water or ethylene glycol. The concentration and diameter of the polystyrene spheres may be adjusted to set the critical shear rate at a desired level. In the embodiment presently preferred, the critical shear rate, established by tests using a cone-and-plate viscometer, is near $1.0\ s^{-1}$. Depending on the application intended for the device, the critical shear rate for suspensions of a given particle diameter might be adjusted to be a factor of 10 larger or smaller by increasing or decreasing the volume fraction of polystyrene spheres. In the preferred embodiment of the invention, the particle diameter is between 0.5 and 2.0 micrometers, and the volume fraction is between 55 and 70 percent. It should be appreciated that in some applications, the dilatant composition within the enclosure 12 is a filled oil or gel, including a silicone gel, dimethylsiloxane gel or putty, or mineral oil, or gel containing particles of silica, celite, polystyrene or other rigid materials.

Figure 8:
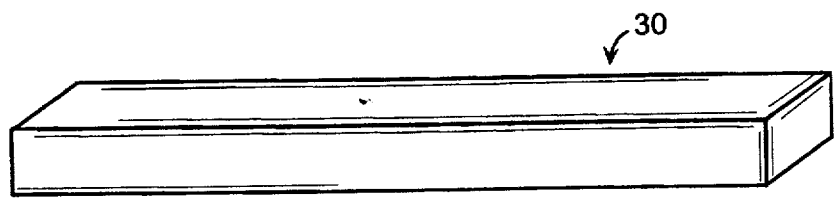
FIG. 8 is a perspective view of an alternate strap embodiment of the present invention.
Figure 9:
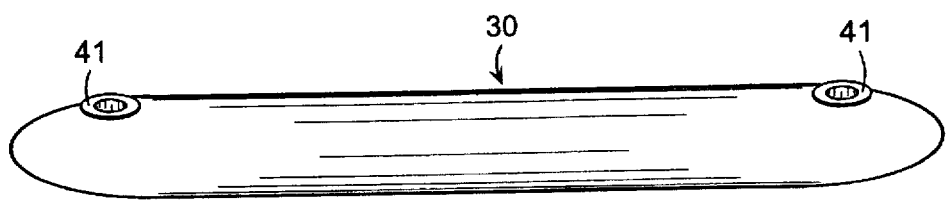
FIG. 9 is a perspective view of another strap embodiment of the invention.
Figure 10:
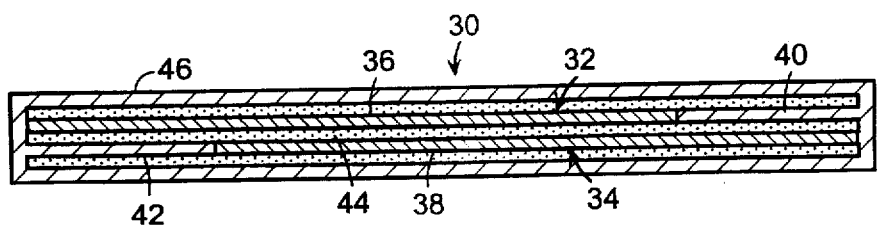
FIG. 10 is a cross-sectional view of the strap of FIG. 8.
Figure 11:
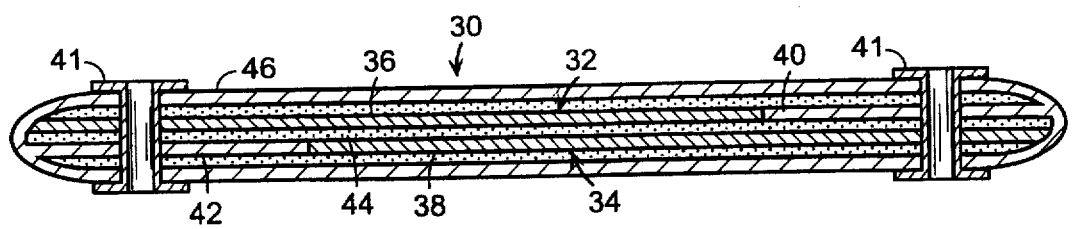
FIG. 11 is a cross-sectional view of the strap of FIG. 9.

Alternate embodiments of the tug-resistant unit of the present invention are illustrated in FIGS. 8 and 9 as strap 30. FIG. 10 and FIG. 11 show that inside the strap 30, a first member 32 and a second member 34 are positioned such that an inextensible portion 36 of the first member 32 overlies an inextensible portion 38 of the second member 34. In accordance with this embodiment, an extensible portion extends from each of the members between the inextensible portion and an end of the strap 30. The first member 32 is coupled to one end of a strap 30 by an extensible portion 40 and the second member 34 is attached to an opposite end of the strap 30 by an extensible portion 42. Between the two members 32 and 34 is a layer of shear-thickening composition 44 similar to a dilatant fluid. The members 32 and 34 and the shear-thickening composition 44 are encompassed within an enclosure such as envelope 46 formed by an extensible material. In the embodiment of FIG. 8, the envelope 46 is formed by rectangular members of extensible material, similar to items 461 and 462 of FIG. 12, that have been joined together along their edges to form the envelope 46. In the embodiment of FIG. 9, a tube of extensible material forms the envelope 46 and has been sealed at its ends.

Figure 12:
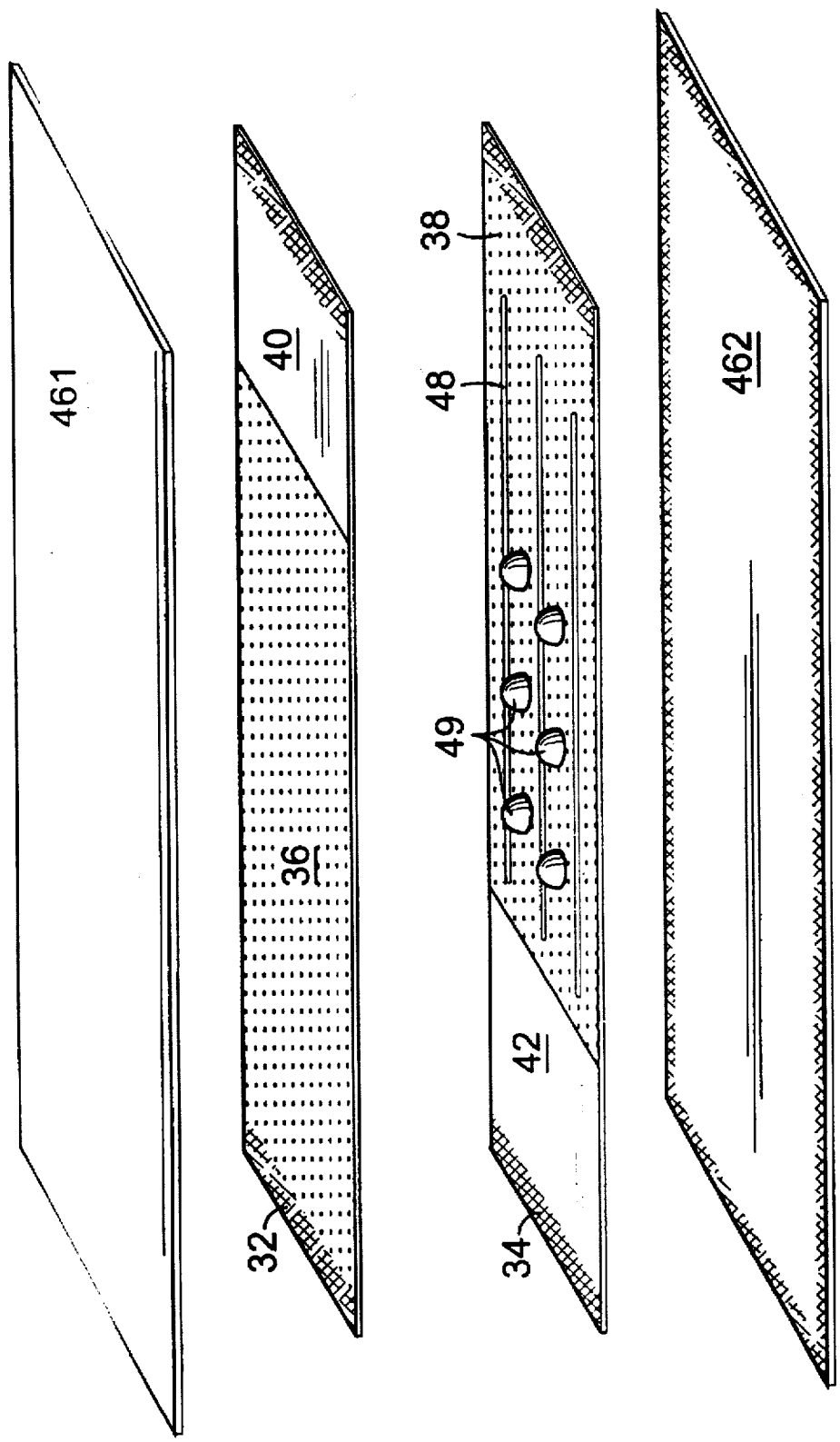
FIG. 12 is an exploded view of the strap of FIG. 8.

Referring now to FIG. 12, a spacer in the form of a series of longitudinal raised ridges 48 projecting from the inextensible portion 38 of the second member 34 maintains a controlled separation between the first and second members 32 and 34. This ensures a volume between the two members 32 and 34 within which the shear-thickening composition 44 can fill. The spacer formed by the longitudinal raised ridges 48 may be provided by any number of projections of any variety of shapes from one or both of the inextensible portions of members 32 and 34. As shown in FIG. 12, the spacer may further include a plurality of protrusions 49 projecting from the inextensible portion 38 of the second member 34. Alternatively, the protrusions 49 may be provided on the inextensible portion 36 of the first member 32, or on both of the inextensible portions 36 and 38. The protrusions 49 and longitudinal raised ridges 48 are provided so that they may additionally act to improve the coupling interaction between the inextensible portions and the shear-thickening composition 44 in the presence of shear stress. Securing means may penetrate through the strap 30 at each end, as shown, for example, in FIGS. 9 and 11, where grommets 41 provide a passage through the ends for receiving bolts, hooks, or other devices for applying a force.

As the inextensible portions 36 and 38 are joined to the extensible envelope 46 by oppositely situated extensible portions 40 and 42 respectively, in the presence of an extending force tending to pull the left and right ends of the strap 30 apart, the extensible portions 40 and 42 stretch while the inextensible portions 36 and 38 contained within the strap 30 do not stretch appreciably. As a result, the inextensible portions 36 and 38 are able to slide past one another in a shearing motion when the end-to-end linear velocity of lengthening is low. However, when the end-to-end velocity of lengthening is large enough to cause the shear-thickening composition 44 between the inextensible portions 36 and 38 to reach its critical shear rate, the viscosity of the composition increases many-fold to oppose the shearing motion between the inextensible portions.

In accordance with one embodiment of the present invention, the extensible portions 40 and 42, and envelope 46 of the strap 30 are preferably made from urethane, neoprene or vinyl rubber of relatively low durometer, preferably between 20 and 60 durometer. The inextensible portions 36 and 38, being preferably flexible, may be made from the flexible inextensible material used for forming the inextensible member 16 and enclosure 12 of strap 10. The inextensible portions 36 and 38 may include surfaces that are sufficiently rough similar to that on the inextensible enclosure 12 and member 16 of strap 10 so as not to slide relative to the shear-thickening composition 44 when subject to the rapidly varying tensile forces. The extensible and inextensible portions of strap 30 may, in an alternate embodiment, be fabricated from the same elastomeric material. In particular, the extensible portions 40 and 42 may be thin or narrow elements of the elastomeric material and the inextensible portions 36 and 38 may be thick or wide elements of the elastomeric material. Alternatively, the inextensible portions 36 and 38 may include fabric or other composite reinforcements in the matrix of the elastomeric material while the extensible portions 40 and 42 may be devoid of such reinforcements.

Figure 13:
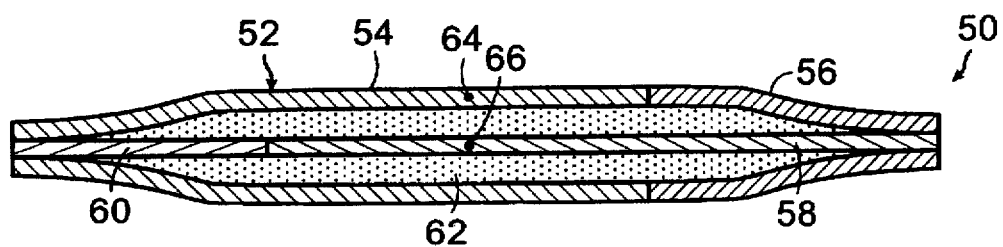
FIG. 13 is a cross-sectional view of another alternative strap embodiment of the invention, shown while in a resting state.
Figure 14:
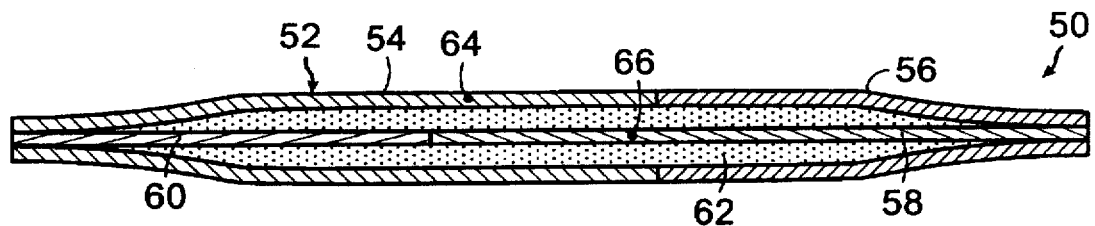
FIG. 14 is a cross-sectional view of the embodiment of FIG. 13 in a stretched state.

An alternate embodiment of the invention is shown in FIGS. 13 and 14. Here, a strap 50 includes an enclosing envelope 52 formed in part by an inextensible portion 54. The envelope is completed by an extensible portion 56. An inextensible tongue 58 is attached to an end of the strap 50. The inextensible tongue 58 extends through the extensible portion 56 of the envelope and into the portion encompassed by the inextensible portion 54. The inextensible tongue 58 is joined by an extensible link 60 to an opposite end of the strap 50. There exists an overlapping region between the inextensible portion 54 forming part of the envelope 52 and the inextensible tongue 58 maintained within the strap 50. A shear-thickening composition 62 exhibiting a dilatant flow property is disposed within the envelope 52 between the outer inextensible portion 54 and the inextensible tongue. The inextensible portion 54 and the inextensible tongue 58 each has a Young's modulus of elasticity that is preferably 10 to 50 times the Young's modulus of the extensible portion 56 and the extensible links 60. The extensible portion 56 on the envelope 52, being elastic, is designed to stretch when the end-to-end length of the strap 50 is increased.

Only for purposes of illustrating the function of the invention, marker dots 64 and 66 are inserted into the drawings of FIG. 13 and FIG. 14. The dots are situated opposite one another in the non-tensioned strap 50 of FIG. 13. The dots are separated, showing relative movement between the inextensible portion 54 and the inextensible tongue 58, upon slow stretching of the strap as shown in FIG. 14. The inextensible portion 54 and inextensible tongue 58 do not stretch, but slide past one another during the slow lengthening of the respective extensible portion 56 and extensive link 60. The shear-thickening composition 62 permits the slow shearing strains attending slowly-varying tensile loads. As the tensile loads are released, the strap 50 recoils to its resting length in response to the elasticity of the extensible portion 56 and extensible link 60. A rapid increase in load causes the shear-thickening composition 62 to increase in viscosity and prevents rapid shearing of the inextensible portion 54 and inextensible tongue 58 past one another. This is felt as a locking of the strap 50.

Figure 15:
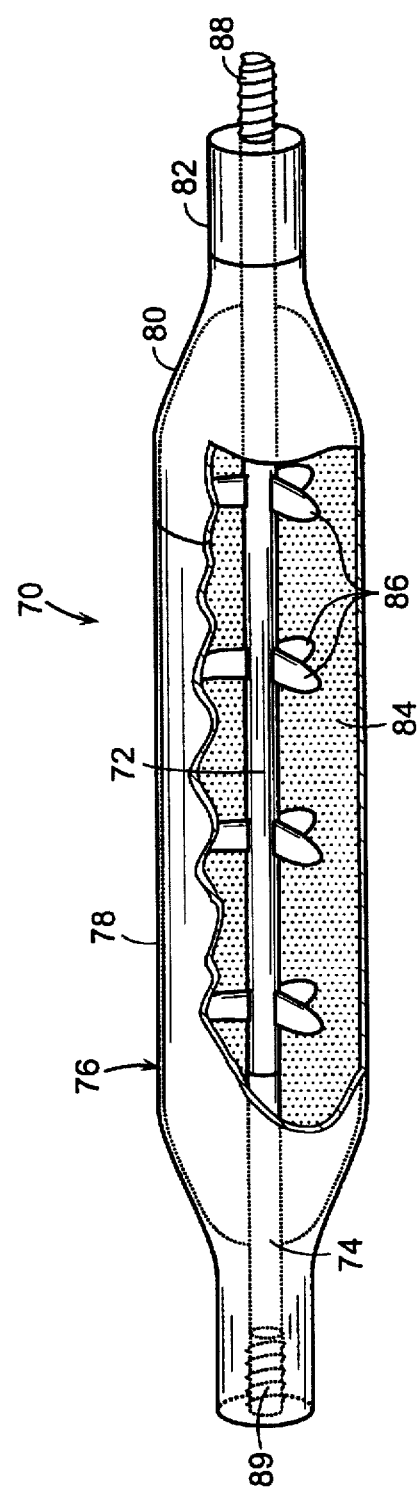
FIG. 15 is a partially broken-away view of a tug-resistant unit of the present invention employing a cylindrical link.

A further embodiment of the tug-resistant unit of the invention is shown in FIG. 15 as a link 70. Link 70 includes a flexible but inextensible rod or cord segment 72 extending from one end of the link 70 toward an opposite end. The inextensible cord segment 72 is joined to an extensible cord segment 74 which extends toward and is joined to the opposite end of the link 70. An enclosing envelope 76 is provided with a flexible but inextensible portion 78 joined to a continuing flexible and extensible portion 80 which terminates in a flexible but inextensible end region 82. The complete envelope made up of the inextensible portion 78, extensible portion 80, and inextensible region 82 encloses the cord segments 72 and 74 to provide an overlap between the inextensible portion 78 of the envelope 76 and the inextensible cord segment 72. The link 70 may also be designed such that the envelope 76 includes only the inextensible portion 78 and the extensible portion 80. However, an inextensible end region 82 is preferred as such a region provides the envelope 76 with added reinforcement when connecting the tug-resistant link 70 to loads or other tug-resistant links. In the embodiment of FIG. 15, a shear-thickening composition 84 having dilatant properties is provided between the cord segments and the envelope. In addition, a plurality of radial projections 86 extends from the inextensible cord segment 72 to maintain a gap of controlled dimensions between the inextensible cord segment 72 and the envelope 76. The radial projections 86 also help to improve coupling between the inextensible cord segment 72 and the inextensible portion 78 of the envelope. At each end of the link 70, means such as a threaded male region 88 and a threaded female region 89 are provided for connecting the tug-resistant link 70 to other tug-resistant links or other external mechanisms for transmitting force to the inextensible portions of the link 70. The means may also include, but are not limited to, holes through each end of the link, eyelets, Velcro®, or other conventional methods of attachment.

With reference to FIG. 16, an alternate embodiment of the tug-resistant link is shown, in cross-sectional view, as a telescoping link 90 having a substantially cylindrical enclosure such as envelope 92. The envelope 92 includes a flexible but inextensible portion 94 and an extensible portion 96. In the presently preferred embodiment, the extensible portion 96 is designed in the manner of a bellows. A substantially cylindrical inextensible member 98, being concentrically disposed within the envelope 92, extends from one end of the envelope through the extensible portion 96 and into the inextensible portion 94 of the envelope 92. An extensible bellows 100 extends from the inextensible member 98 and is connected to an opposite end of the envelope 92. A shear-thickening composition is disposed within the envelope 92 about the inextensible member 98. As shown in the figures, projecting elements 102 may be provided to maintain a separation between the envelope 92 and the inextensible member 98. Although shown to be positioned on the inextensible portion 94 of the envelope 92, the projecting elements 102 may alternatively be positioned on the inextensible member 98, or on both the member and the envelope 92 so long as the elements 102 act to maintain a separation therebetween. The present link 90 may be used as a tug-resistant element between two rigid cylinders of a telescoping joint. By coupling the inextensible portion 94 to an outer cylinder and the inextensible member 98 to an inner cylinder of the telescoping joint, in the presence of a low end-to-end linear force applied to the telescoping link 90, the inextensible portion 94 and the inextensible member 98 tend to slide past one another so as to stretch the extensible bellows portion 96 and the extensible bellows 100. When the end-to-end linear force is discontinued, the extensible bellows portion 96 and bellows 100 recoil to pull the inextensible portion 94 and member 98 to their respective positions as seen in FIG. 16.

Figure 17:
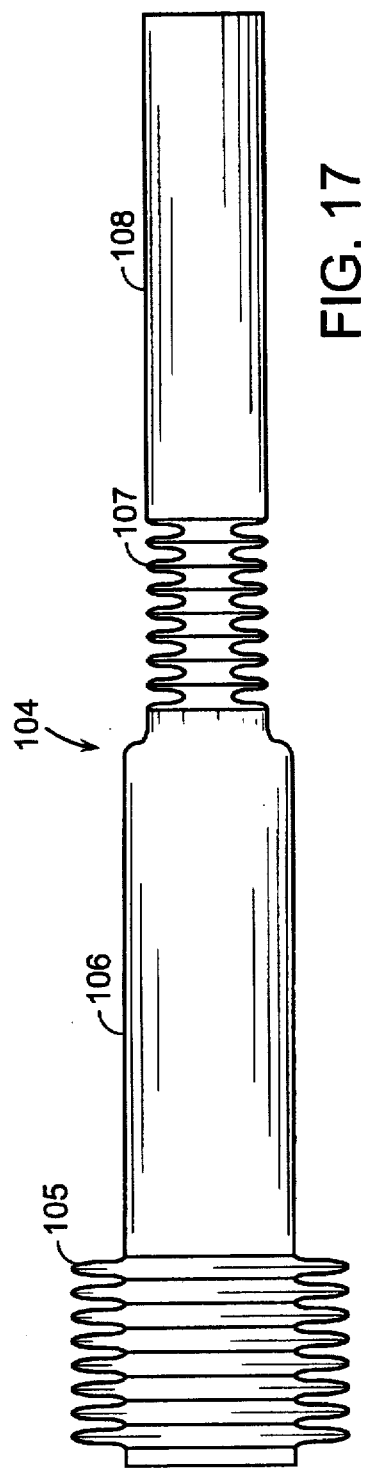
FIG. 17 is a side view of a mold for forming the embodiment of FIG. 16.

The telescoping link 90 of the present embodiment is preferably formed by using a mold 104 of FIG. 17 to provide a closed unit. The mold 104 includes a first fin portion 105, a first substantially cylindrical portion 106, a second fin portion 107, and a second substantially cylindrical portion 108 having a smaller diameter than the first cylindrical portion 106. In one method of manufacture, the mold 104 is first dipped into a container of, for example, vinyl solution. After allowing the vinyl solution to adhere to the mold 104, the mold is removed and the solution allowed to cure and dry on the mold 104. The entire unit is subsequently pulled off the mold 104 and the segment on the unit conforming to the second cylindrical portion 108 is then pushed within the segment conforming to the first cylindrical portion 106 to produce the link 90 of FIG. 16. In particular, the fin portions 105 and 107 on mold 104 give rise to extensible bellows portion 96 and bellows 100 respectively, and the cylindrical portions 106 and 108 give rise to inextensible portion 94 and member 98 respectively.

Figure 18:
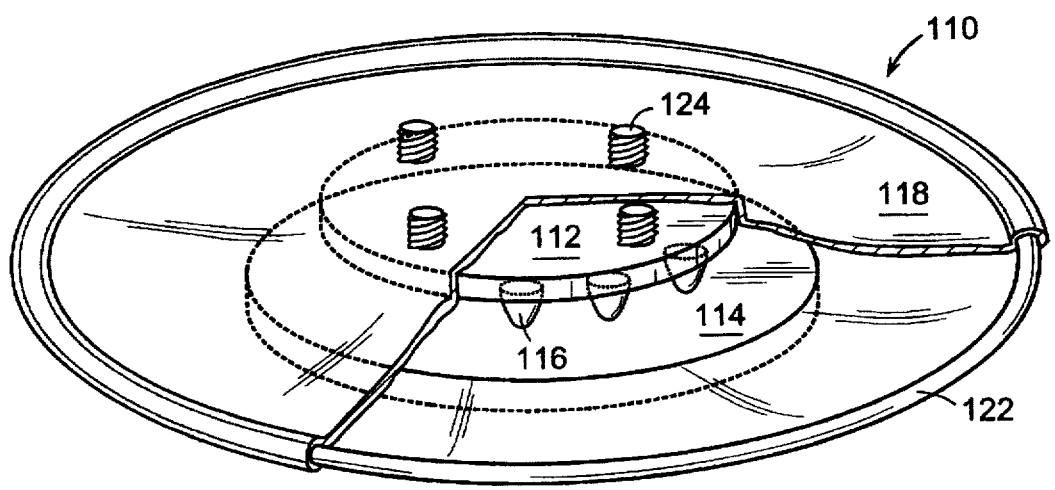
FIG. 18 is a partially broken-away perspective view of a sliding hinge embodiment of the invention.
Figure 19:
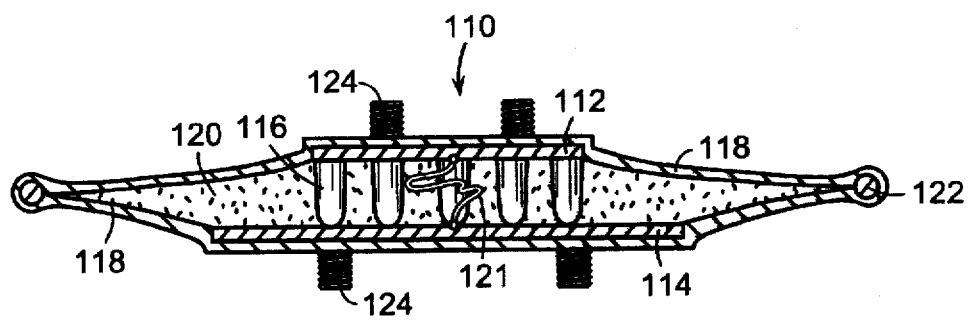
FIG. 19 is a cross-sectional view of the embodiment of FIG. 18.
Figure 20:
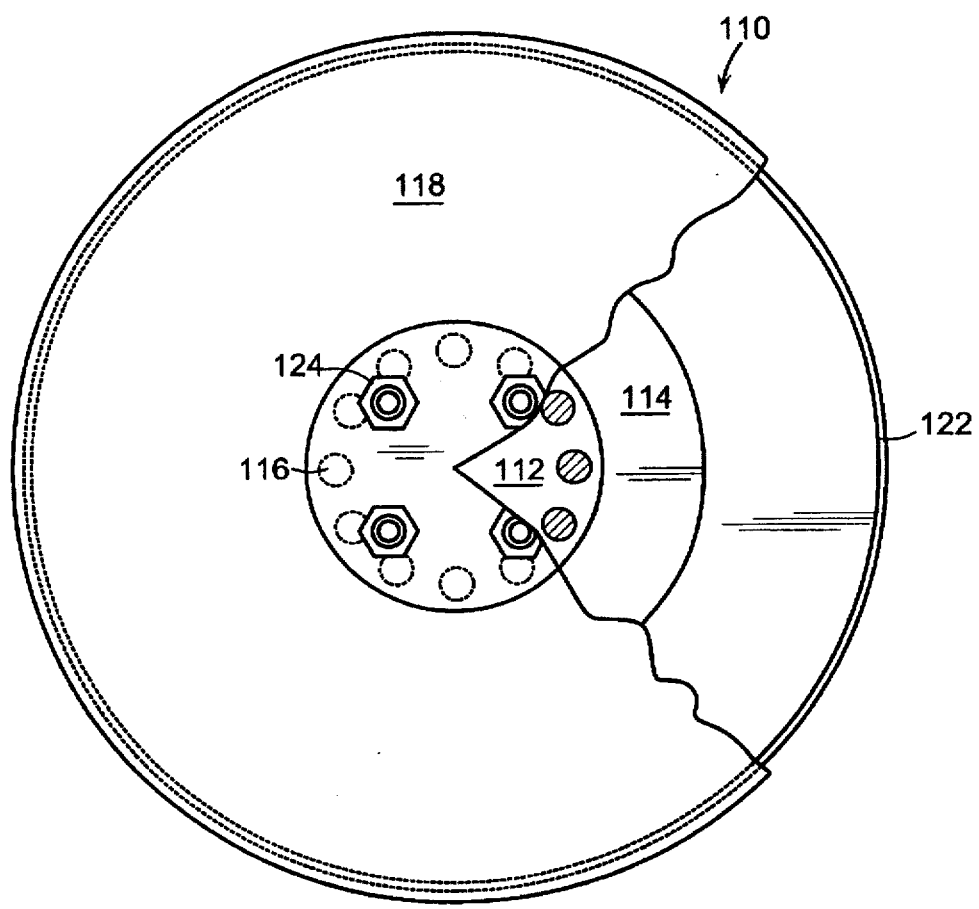
FIG. 20 is a partially broken-away top view of the embodiment of FIG. 18.

Another configuration of the invention is depicted in FIG. 18 and elaborated in FIGS. 19 and 20 as a sliding and rotating joint 110. The joint 110 includes flexible but inextensible plates 112 and 114 which are maintained generally parallel to one another and in spaced apart relation by a plurality of projections 116 and/or a series of ridges extending from one or both of the inextensible plates. In one embodiment of the invention, the top inextensible plate 112 may include a smaller diameter than the bottom inextensible plate 114, as provided in FIGS. 19 and 20. However, it should be appreciated that the top and bottom plates may also be designed to include substantially similar diameters. A flexible and extensible membrane forms an enclosing envelope 118 to which plates 112 and 114 are joined. The enclosing envelope 118 provides a space within which a shear-thickening composition 120 may occupy. In the presence of the shear-thickening composition 120, the projections 116 and/or ridges may act to improve the coupling between the inextensible plates and the shear-thickening composition. The joint 110 may further include one or more inextensible rings 122 at the periphery of the envelope 118. The ring 122, which defines the outer margin of envelope 118, acts to hold the envelope 118 in an extended manner. Threaded studs 124 may be provided on the inextensible plates 112 and 114 for securing objects to the joint 110. Alternatively, threaded studs 124 may be replaced by other conventional securing means including clips, snaps, Velcro® fasteners, threaded holes for screws, and the like.

The configuration depicted in FIGS. 18–20 permits a modest degree of translation and rotation of plate 112 relative to plate 114 when a slowly-varying force acts on one plate with respect to the other to distort the flexible envelope 118. When the force is removed, each plate returns to its original position as distortions in the extensible envelope 118 relax. When a rapidly-varying force acts between the two plates, the shear-thickening composition 120 between the plates resists the resulting rapidly shearing motions and allows only slow translation and rotation of one plate with respect to the other. Normal forces tending to push the two plates together are resisted by the rigid projections 116. Normal forces tending to pull the two plates 112 and 114 apart are resisted by the constant-volume property of the composition 120 within the closed envelope 118. Furthermore, an inextensible cord 121, connecting plates 112 and 114, may be provided to impose a maximum limit on the gap between the plates.

Figure 21:
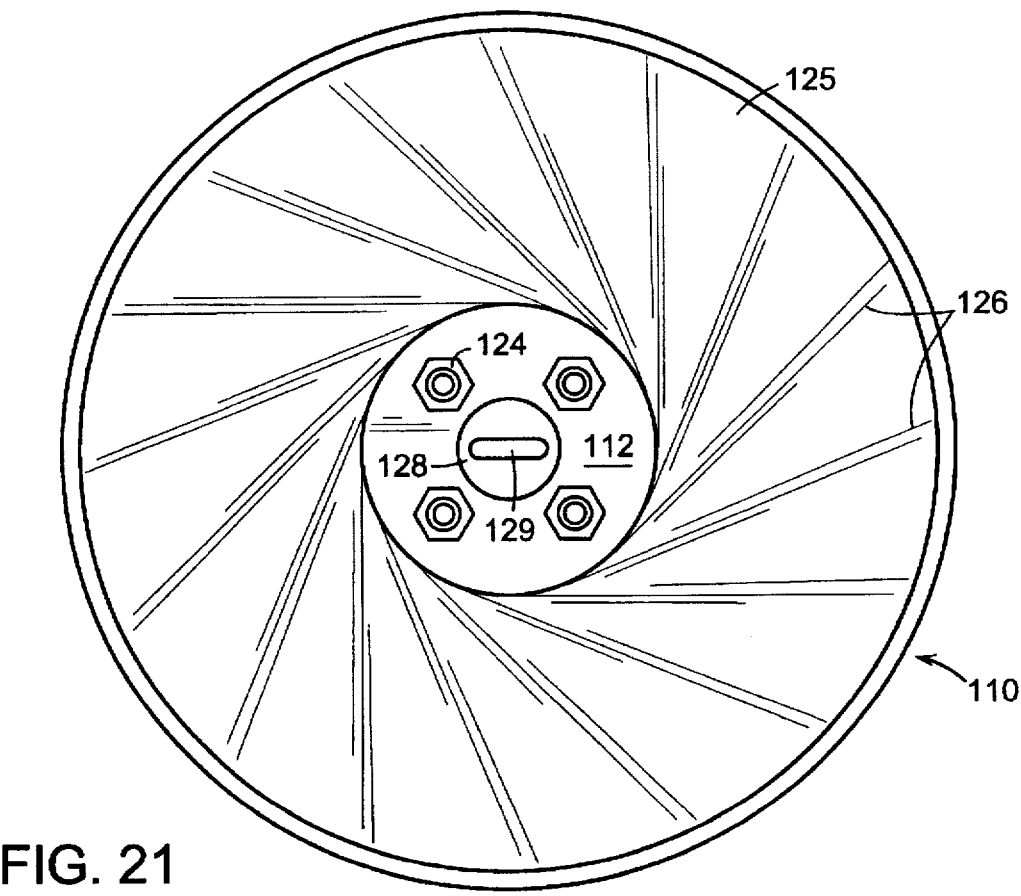
FIG. 21 is a top view of another alternate embodiment of FIG. 18.

Referring now to FIG. 21, the extensible envelope of joint 110 may alternatively be substituted with a flexible inextensible envelope 125. To permit translational and rotational movement of one inextensible plate with respect to the other inextensible plate, the flexible inextensible envelope 125 is provided with a plurality of folds 126. The folds 126, in the presence of a slowly-varying external force acting on one of the plates, can fold or unfold, depending on the direction of the force, to allow rotational motion of one plate relative to the other in either a counter-clockwise or clockwise direction. Once the slowly-varying external force is removed, the flexible inextensible envelope 125 may recoil to reform the folds 126 thereby permitting each of the plates 112 and 114 to return to its original position. An elastic band (not shown), similar to a latex rubber band, may be used in place of the inextensible cord 121 of FIG. 19 to aid each of the plates 112 and 114 to return to its original position. A cover 128 may be provided on the top inextensible plate 112 of the hinge embodiment of FIGS. 18–20. The cover 128 preferably includes a slot 129 to allow removal of the cover 128 for access within the interior of joint 110.

Turning to FIGS. 22 and 23, an embodiment of the invention uses the bending stiffness of beams, rather than the elongation of an extensible member, to obtain a restoring force. In FIG. 22, a double-beam structure 130 is shown having inextensible but flexible beam elements 132 and 134. The top beam 132 and the bottom beam 134 are maintained in parallel relationship by ridges or protrusions 136 extending from one of the beams 132. The space between the beams is occupied by a shear-thickening composition 138 having dilatant properties. A flexible and extensible membrane encloses beams 132 and 134 to provide an envelope 140 for the shear-thickening composition. The left end of the double-beam structure 130 is shown built into a wall 141, but an alternative construction would be one where FIG. 22 shows half of a double-beam structure whose mid-point occurs where the wall 141 is presently. When a slowly-varying force F acts in a transverse direction as shown in FIG. 23, the shear-thickening composition 138 permits a shearing motion to occur between the beams 132 and 134, and a substantial deflection of the right-hand end of the structure occurs. On the other hand, if a rapidly-varying force acts in the same direction at the same place, the shear-thickening composition resists rapid shearing motions, with the net effect being that bending deflections of the end of the structure are markedly reduced.

In an alternative configuration, the inextensible beams 132 and 134, shown in FIGS. 24 and 25, are not enclosed within the flexible and extensible envelope 140. Rather, the extensible envelope 140 is designed to enclose only the shear-thickening composition 138. To maintain the shear-thickening composition 138 between the inextensible beams 132 and 134 so that rapid shearing motions may be resisted, the envelope 140 is preferably bonded (e.g. adhesive bonded) to the inextensible top beam 132 and bottom beam 134 of the double beam structure 130. Of course, other bonding methods may also be employed so long as such methods are capable of maintaining the envelope 140 containing the shear-thickening composition 138 between the inextensible beams. From the perspective of FIG. 25, when a slowly-varying force F acts in a transverse direction relative to the right end of the double-beam structure 130, the shear-thickening composition 138 permits a shearing motion between a bottom layer and the top layer of the flexible envelope 140. Because the bottom layer of the envelope is bonded to the bottom beam 134 of the current embodiment, the shearing motion is transferred to the bottom beam 134 thereby allowing the bottom beam 134 to slide with respect to the top beam 136 resulting in a substantial deflection of the free right hand side of the structure. When a rapidly-varying force is applied to the free right end of the double-beam structure 130, the protrusions 136 act with the shear-thickening composition 138 to resist a shearing motion between the bottom and top layers of the envelope 140. In this manner, a shearing motion between the bottom beam 134 and the top beam 132 are also resisted.

With specific reference to FIG. 26, a cavity 142 may be provided at each end of the double-beam structure 130 to lower the incidence of the envelope 140 tearing during shearing motions. In particular, as with some configurations, the flexible envelope 140 may be bonded along its entire length to the inextensible top beam 132 and bottom beam 134 (see FIGS. 24 and 25). As a result, this leaves the envelope 140 with only a small area 144 at its tip along which the flexible envelope 140 may extend. In the presence of extreme shearing motions, such a small area may not be enough for the envelope 140 to sufficiently extend. In the embodiment of FIG. 26, the entire perimeter portion of the envelope 140 within the cavity 142 is not bonded to either of the beams. To this end, the envelope 140 is provided with a much larger area along which it may extend in the presence of a shearing displacement. As the ends of the double-beam structure 130 are not bonded to the envelope 140 to accommodate the stretching of the envelope within the cavity 142, a retaining clip 144 may be provided at the ends of the structure 130 to maintain an approximation between the inextensible top beam 132 and bottom beam 134.

Figure 27:
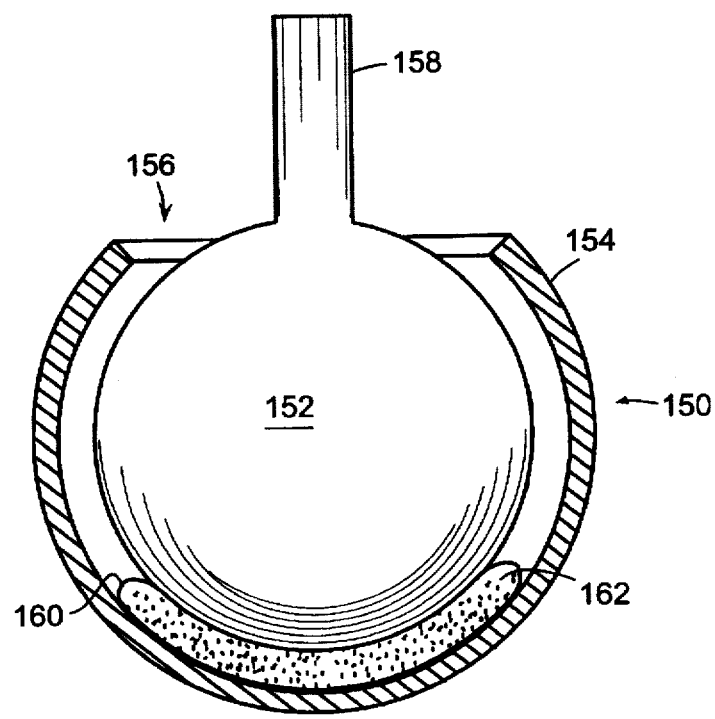
FIG. 27 is a cross-sectional view of an embodiment of the invention employing a ball and socket wherein the ball is in a rest position.
Figure 28:
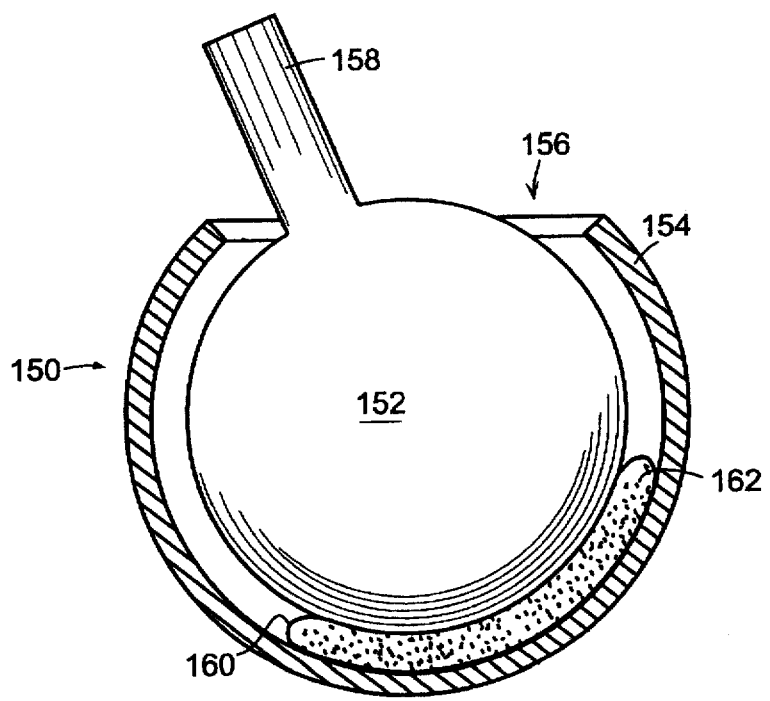
FIG. 28 is a cross-sectional view of the embodiment of FIG. 27 after the ball has been rotated from the rest position within the socket.

A further embodiment of the tug-resistant unit of the present invention can be seen in FIGS. 27 and 28 in the form of a ball and socket joint 150. The joint 150 comprises a rigid ball 152 disposed within a rigid and substantially spherical enclosure 154. The enclosure 154 includes an opening 156 through which an elongated member 158, being securely mounted to the rigid ball 152, extends. The opening 156 permits pivotal movement of the rigid ball 152 within the enclosure about the X, Y and Z axes (not shown) when a force is applied to the member 158. The opening 156 further permits rotational movement of the rigid ball 152 relative to the enclosure 154. The joint 150 also includes an enclosed membrane 160 interposed between the rigid ball 152 and the enclosure 154. The membrane 160 is enclosed so as to retain a shear-thickening composition 162 therein. As illustrated in FIGS. 27 and 28, one surface of the membrane 160 is attached to an area about the periphery of the rigid ball 152, while an opposite surface on the extensible membrane 160 is attached to a corresponding area on the enclosure 154. Such an attachment to the ball and enclosure permits the membrane 160 to roll, fold, stretch, or otherwise deform to allow movement of the rigid ball 152 relative to the enclosure 154 when a slowly-varying force is applied to the member 158, but to resist any relative movement when a rapidly-varying force is applied to the member 158. When the slowly-varying force is no longer applied to the member 158, the elasticity within the membrane 160, or a separate elastic link, allows the membrane to return to its previous condition, thereby pulling the ball 152 and thus the member 158 back to the resting condition displayed in FIG. 27. Attachment of the membrane 160 to the rigid ball 152 and enclosure 154 may be accomplished by any means well known in the art, for example, adhesive bonding.

It should be appreciated that various changes, modifications, and alterations of the embodiments provided within this application are contemplated by those skilled in the art without departing from the scope of the present invention. For example, the strap and joint embodiments of the present invention may be modified so that the inextensible members are axisymmetric so that not only are the inextensible members capable of translational movement, but are also capable of axially rotatable movement relative to one another. Such a modification may similarly be made to the beam and ball-and-socket embodiments of the present invention.

The embodiments depicted in FIGS. 1, 8–9, 13, and 15 may advantageously be used, for example, as chin straps for helmets. Another application for these embodiments would be for closing the foot into a shoe or boot. Such an application could protect a foot against inversion sprains. There is also the prospect of obtaining enhanced performance in sports where a ball is kicked by a shoe as in American football and soccer by using the device to stiffen the dorsal surface of the shoe to achieve a better transfer of kinetic energy from the foot to the ball by reducing the energy lost as the shoe and foot deform under the impact with the ball. An embodiment which resists both rotation and translation on impact may be used in safety or duty shoes whose object is to allow comfortable deformations of one semi-rigid portion of a shoe with respect to another during ordinary walking but to protect the foot from impacts caused by falling tools or from other potentially injurious accidents. The invention may be used to form strap or joint devices connecting plate elements of protective pads. The invention may further be used as coupling devices between semi-rigid elements in knee braces, wrist or elbow stiffeners and cervical collars. Straps according to the invention may be formed into a restraining glove to be worn by a surgeon or an operator performing a delicate piece of handwork. The invention could therefore damp physiological tremor while permitting the relatively slower motions required for the work operation. In addition, there may be industrial applications for the invention including crash-locking shoulder strap or seat belt restraint mechanisms, industrial padding and packaging. The invention may also have motion control applications. For example, the ball and socket embodiment depicted in FIGS. 27 and 28 may be utilized as a joy-stick control in precision motion devices which may require relatively slow operation of the control. The variety of applications that are available for use of the invention providing a link with low resistance to slowly-varying translational and rotational forces but high resistance to large, rapidly varying forces are enormous.

What is claimed is:

1. A tug-resistant unit comprising:
    a first member having an inextensible portion and a surface;
    a second member having an inextensible portion overlapping the surface of said first member and arranged for translational movement substantially parallel to the surface of said first member; and
    a shear-thickening composition disposed between said first member and said second member so as to apply a variable resistance to translational movement of said second member relative to said first member as a function of shear forces exerted upon said shear-thickening composition.

2. The unit of claim 1 further comprising extensible member means for completing an enclosure to hold said shear-thickening composition therein.

3. The unit of claim 1 wherein the inextensible portion of each of the first and second members extends an entire length of each of the first and second members.

4. The unit of claim 1 wherein the first member further includes an extensible portion extending from one end of the first member.

5. The unit of claim 4 wherein the second member further includes an extensible portion extending from one end of the second member.

6. The unit of claim 1 wherein said shear-thickening composition is a dilatant fluid exhibiting an immediate increase in viscosity in response to a shear force to the unit.

7. The unit of claim 1 wherein said shear-thickening composition is a dilatant gel exhibiting an immediate increase in viscosity in response to a shear force to the unit.

8. The unit of claim 1 further comprising a spacer between the inextensible portion of each of said first and second members to maintain a volume between said members for said shear-thickening composition.

9. The unit of claim 8 wherein said spacer comprises a series of longitudinal raised ridges projecting from one of said inextensible portions of said first and second members so as to maintain a controlled separation between said first and second inextensible members.

10. The unit of claim 8 wherein said spacer comprises a plurality of protrusions projecting from one of said inextensible portions of said first and second members so as to enhance coupling between the inextensible portions and the shear-thickening composition.

11. A tug-resistant unit comprising:
   a first member having an inextensible portion and a surface;
   a second member having an inextensible portion overlapping the surface of said first member and arranged for shearing movement with respect to the surface of said first member;
   a shear-thickening composition disposed between said first member and said second member so as to apply a variable resistance to shearing movement of said second member relative to said first member as a function of shear forces exerted upon said shear-thickening composition; and
   an enclosure for holding said shear-thickening composition therein and connected to said first and second members so as to return said first and second members to a non-tensioned state with respect to one another after removal of an external force that has moved said members with respect to one another.

12. The unit of claim 11 wherein the inextensible portion of each of the first and second members extends an entire length of each of the first and second members.

13. The unit of claim 11 wherein the first member further includes an extensible portion extending from one end of the first member.

14. The unit of claim 13 wherein the second member further includes an extensible portion extending from one end of the second member.

15. The unit of claim 11 wherein said shear-thickening composition is a dilatant fluid exhibiting an immediate increase in viscosity in response to a shear force to the unit.

16. The unit of claim 11 wherein said shear-thickening composition is a dilatant gel exhibiting an immediate increase in viscosity in response to a shear force to the unit.

17. The unit of claim 11 further comprising a spacer between the inextensible portion of each of said first and second members to maintain a volume between said members for said shear-thickening composition.

18. The unit of claim 17 wherein said spacer comprises a series of longitudinal raised ridges projecting from one of said first and second inextensible members so as to maintain a controlled separation between said first and second inextensible members.

19. The unit of claim 17 wherein said spacer comprises a plurality of protrusions projecting from one of said inextensible portions of said first and second members so as to enhance coupling between the inextensible portions and the shear-thickening composition.

20. The unit of claim 11 wherein said inextensible portion of each of said first and second members is flexible.

21. The unit of claim 11 wherein said first and second members comprise first and second inextensible plates.

22. The unit of claim 21 further comprising a spacer between said first and second inextensible plates to maintain a volume between said plates for said shear-thickening composition.

23. The unit of claim 22 wherein said spacer comprises a plurality of protrusions projecting from one of said first and second inextensible plates so as to enhance coupling between the inextensible plates and the shear-thickening composition.

24. The unit of claim 21 wherein said first and second inextensible plates are flexible.

25. The unit of claim 21 wherein said shear-thickening composition is a dilatant fluid exhibiting an immediate increase in viscosity in response to a shear force to the unit.

26. The unit of claim 21 wherein said shear-thickening composition is a dilatant gel exhibiting an immediate increase in viscosity in response to a shear force to the unit.

27. The unit of claim 21 wherein said enclosure comprises an extensible envelope containing both inextensible plates and said shear-thickening composition disposed between said plates.

28. The unit of claim 21 wherein said enclosure comprises a flexible inextensible envelope containing both inextensible plates and said shear-thickening composition disposed between said plates.

29. The unit of claim 11 wherein said first member comprises an inextensible ball and said second member comprises an inextensible socket within which said ball is disposed.

30. The unit of claim 29 wherein said inextensible ball and inextensible socket are rigid.

31. The unit of claim 29 wherein said shear-thickening composition is a dilatant fluid exhibiting an immediate increase in viscosity in response to a shear force to the unit.

32. The unit of claim 29 wherein said shear-thickening composition is a dilatant gel exhibiting an immediate increase in viscosity in response to a shear force to the unit.

33. A tug-resistant unit comprising:
   a first member having an inextensible portion and a surface;
   a second member having an inextensible portion overlapping the surface of said first member and arranged for shearing movement with respect to the surface of said first member;
   a shear-thickening composition disposed between said first member and said second member so as to apply a variable resistance to shearing movement of said second member relative to said first member as a function of shear forces exerted upon said shear-thickening composition; and
   an enclosure for holding said shear-thickening composition therein and connected to said first and second members.

34. The unit of claim 33 further comprising a spacer between said first and second inextensible beams to maintain a volume between said beams for said shear-thickening composition.

35. The unit of claim 34 wherein said spacer comprises a plurality of protrusions projecting from one of said first and second inextensible beams so as to enhance coupling between the inextensible beams and the shear-thickening composition.

36. The unit of claim 33 wherein said first and second inextensible beams are flexible.

37. The unit of claim 33 wherein said shear-thickening composition is a dilatant fluid exhibiting an immediate increase in viscosity in response to a shear force to the unit.

38. The unit of claim 33 wherein said shear-thickening composition is a dilatant gel exhibiting an immediate increase in viscosity in response to a shear force to the unit.

39. The unit of claim 33 wherein said enclosure comprises an extensible envelope containing both inextensible beams and said shear-thickening composition disposed between said beams.

40. The unit of claim 33 further comprising means for maintaining approximation between said first and second inextensible beams.

41. A strap comprising:

an elongated extensible enclosure;

a first member having an inextensible portion connected to a first end of said elongated enclosure;

a second member having an inextensible portion connected to a second end of said elongated enclosure opposite from the first end and extending within said enclosure so as to overlap said first inextensible member; and a shear-thickening composition enclosed within said enclosure and between said first and second inextensible members.

42. The strap of claim 41 wherein said first and second inextensible members have a Young's modulus between 10 and 50 times as large as a Young's modulus of said extensible enclosure.

43. The strap of claim 41 wherein the first inextensible member is further connected to the second end of said elongated enclosure by a first extensible portion and the second inextensible member is further connected to the first end of the elongated enclosure by a second extensible portion.

44. The strap of claim 41 wherein said shear-thickening composition is a dilatant fluid exhibiting an immediate increase in viscosity in response to a shear force to the strap.

45. The strap of claim 41 wherein said shear-thickening composition is a dilatant gel exhibiting an immediate increase in viscosity in response to a shear force to the strap.

46. A strap comprising:

an elongated enclosure having an inextensible portion and an extensible portion;

a member having an inextensible portion and extending from one end of said enclosure through the extensible portion of said enclosure and into the inextensible portion of said elongated enclosure; and a shear-thickening composition disposed between said inextensible member and the inextensible portion of said enclosure.

47. The strap of claim 46 wherein the member further includes an extensible portion extending between the inextensible portion of the member and an end opposite said one end of said enclosure.

48. The strap of claim 46 wherein the inextensible portion of each of said enclosure and said member is flexible.

49. The strap of claim 46 wherein said shear-thickening composition is a dilatant fluid exhibiting an immediate increase in viscosity in response to a shear force to the strap.

50. The strap of claim 46 wherein said shear-thickening composition is a dilatant gel exhibiting an immediate increase in viscosity in response to a shear force to the strap.

51. The strap of claim 46 further comprising a spacer between the inextensible portion of each of said enclosure and said member to maintain a volume therebetween for said shear-thickening composition.

52. The strap of claim 51 wherein said spacer comprises a plurality of protrusions projecting from one of said inextensible portions of said enclosure and said member so as to enhance coupling between the inextensible portions and the shear-thickening composition.

53. A tug-resistant unit comprising:

an elongated inextensible enclosure;

an inextensible member extending from within said inextensible enclosure for translational movement of said member relative to said inextensible enclosure;

means for connecting said inextensible member to an end within said inextensible enclosure; and a shear-thickening composition disposed between said inextensible enclosure and said inextensible member so as to apply variable resistance to translational movement of said member relative to said enclosure as a function of shear forces exerted upon said shear-thickening composition.

54. The unit of claim 53 wherein means for connecting includes an inextensible flexible element.

55. The unit of claim 54 wherein means for connecting further includes an elastic band.

56. The unit of claim 53 wherein said shear-thickening composition is a dilatant fluid exhibiting an immediate increase in viscosity in response to a shear force to the unit.

57. The unit of claim 53 wherein said shear-thickening composition is a dilatant gel exhibiting an immediate increase in viscosity in response to a shear force to the unit.

* * * * *